US007857769B2

(12) United States Patent
Ortiz-Burgos

(10) Patent No.: US 7,857,769 B2
(45) Date of Patent: Dec. 28, 2010

(54) SYSTEM AND METHOD FOR NON-INVASIVELY DETERMINING A LEFT VENTRICULAR END-DIASTOLIC PRESSURE

(76) Inventor: Alejandro Ortiz-Burgos, 339 Catalonia Ave., Coral Gables, FL (US) 33134

( * ) Notice: Subject to any disclaimer, the term of this patent is extended or adjusted under 35 U.S.C. 154(b) by 1493 days.

(21) Appl. No.: 11/166,600

(22) Filed: Jun. 24, 2005

(65) Prior Publication Data

US 2006/0264764 A1  Nov. 23, 2006

Related U.S. Application Data

(60) Provisional application No. 60/682,280, filed on May 18, 2005.

(51) Int. Cl.
*A61B 5/00* (2006.01)
(52) U.S. Cl. ........................ 600/485; 600/500
(58) Field of Classification Search ................ None
See application file for complete search history.

(56) References Cited

U.S. PATENT DOCUMENTS

| 4,203,451 | A | 5/1980 | Panico |
| 5,178,151 | A | 1/1993 | Sackner |
| 6,149,595 | A | 11/2000 | Seitz et al. |
| 6,277,078 | B1 | 8/2001 | Porat et al. |
| 6,379,303 | B1 | 4/2002 | Seitz et al. |
| 6,610,018 | B1 * | 8/2003 | McIntyre ............. 600/485 |
| 6,674,879 | B1 | 1/2004 | Weisman et al. |
| 6,682,485 | B2 | 1/2004 | Seitz et al. |
| 6,708,055 | B2 | 3/2004 | Geiser et al. |
| 2004/0029827 | A1 | 2/2004 | Kawashima et al. |
| 2004/0254483 | A1 | 12/2004 | Zdeblick et al. |
| 2005/0137626 | A1 * | 6/2005 | Pastore et al. .............. 607/3 |

FOREIGN PATENT DOCUMENTS

| WO | WO 98/20791 A1 | 5/1998 |
| WO | WO 03/037181 A2 | 5/2003 |

OTHER PUBLICATIONS

R.S. Wiener et al.; *Trends in the Use of the Pulmonary Artery Catheter in the United States. 1993-2004*; The Journal of the American Medical Association, Jul. 25, 2007, vol. 298, No. 4; pp. 423-429.

(Continued)

*Primary Examiner*—Robert L Nasser
(74) *Attorney, Agent, or Firm*—SNR Denton US LLP

(57) ABSTRACT

A system and method for determining a left ventricular end-diastolic pressure of blood within a left ventricle of a patient includes non-invasively measuring a plurality of cardiac parameters of the patient. The cardiac parameters may include a mitral valve area, and at least one of a stroke volume of the left ventricle, a left ventricular diastolic filling time, and a maximum velocity of blood entering the left ventricle. The systems and methods further include a step of calculating the left ventricular end-diastolic pressure using the measured cardiac parameters.

33 Claims, 3 Drawing Sheets

OTHER PUBLICATIONS

Gordon D. Rubenfeld et al.; *The Pulmonary Artery Catheter*, 1967-2007; The Journal of the American Medical Association, Jul. 25, 2007, vol. 298, No. 4; pp. 458-461.

Derek C. Angus, M.D., MPH; *Caring for the Critically Ill Patient*; The Journal of the American Medical Association, Jul. 25, 2007, vol. 298, No. 4; pp. 456-458.

"Medical Policy—Medicine Section—Non-Invasive Measurement Of Left Ventricular End Diastolic Pressure (LVEDP) in the Outpatient Setting"; Blue Cross and/or Blue Shield, The Regence Group (Date of Origin—Jan. 7, 2005); retrieved from the Internet at URL: <http://blue.regence.com/trgmedpol/medicine/med118.html> (3 pages).

Sharma, G.V.R.K. et al. "Evaluation Of A Noninvasive System For Determining Left Ventricular Filling Pressure"; Arch Intern Med, vol. 162, Oct. 14, 2002 (5 pages).

McIntyre, Kevin M., et al.; "Validation And Clinical Applications Of A Non-Invasive Valsalva Response Recorder"; Journal Of Applied Cardiology, vol. 2, No. 2, pp. 137-169, 1987 (33 pages).

PCT International Search Report dated Dec. 8, 2006 for International Application No. PCT/US06/18954.

* cited by examiner

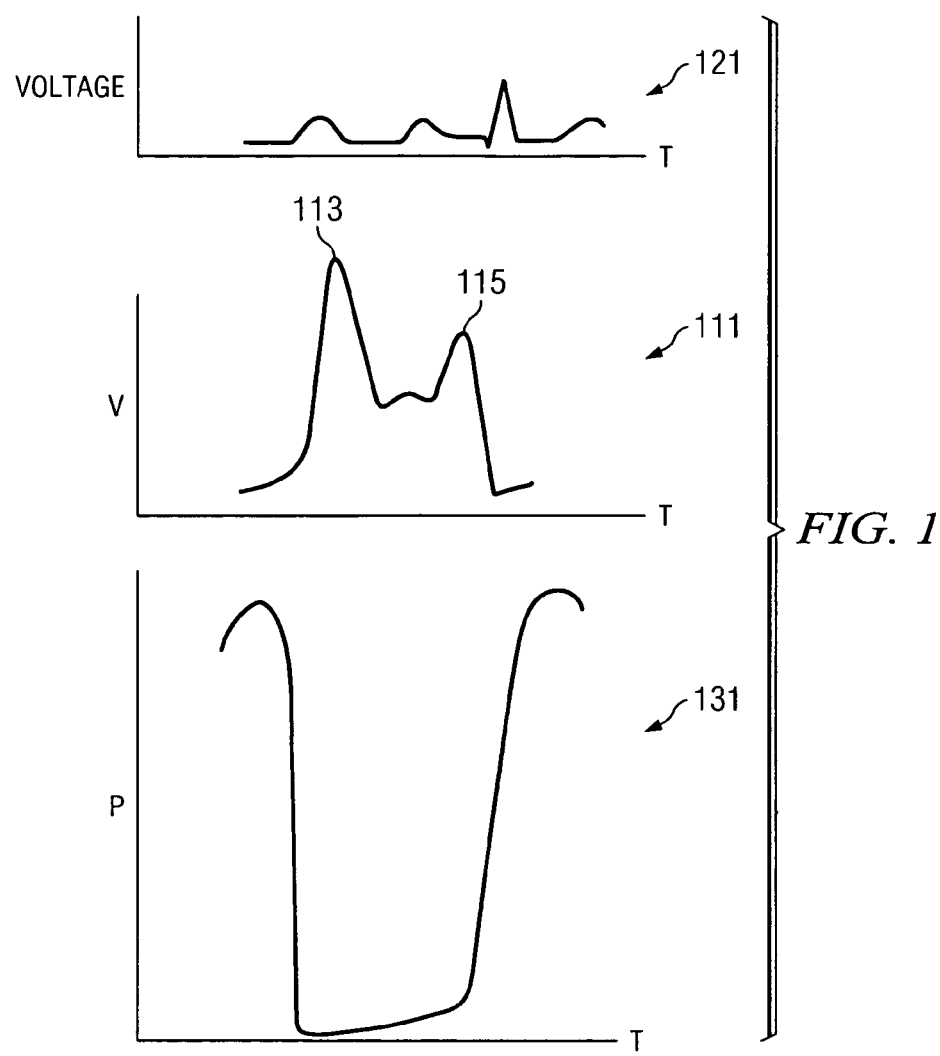
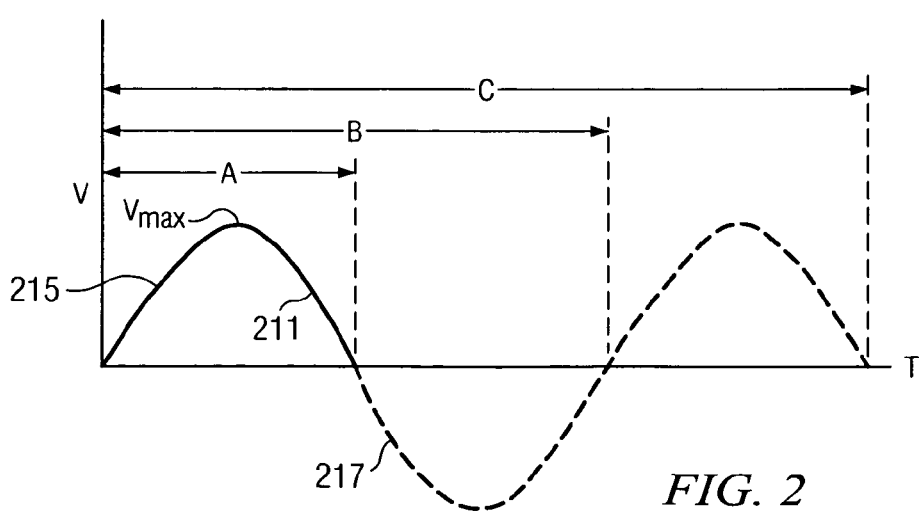
FIG. 1
FIG. 2

SYSTEM AND METHOD FOR NON-INVASIVELY DETERMINING A LEFT VENTRICULAR END-DIASTOLIC PRESSURE

CROSS-REFERENCE TO RELATED APPLICATIONS

This application claims the benefit of U.S. Provisional Application No. 60/682,280, filed May 18, 2005, which is hereby incorporated by reference.

BACKGROUND OF THE INVENTION

1. Field of the Invention

The present invention relates generally to the determination of physiological functions and parameters and more specifically to systems and methods for non-invasively measuring left ventricular pressures of the blood within a left ventricle of a heart.

2. Description of Related Art

The function of the heart is well understood due in large part to the advanced measurement techniques available to cardiologists and other medical professionals. Many parameters of the cardiac cycle may be measured and monitored to determine the general well being of a patient. Some of the monitoring and measurement techniques are invasive, requiring sensors or other measurement devices to be placed within the heart or vessels connected to the heart, while other techniques are non-invasive.

Some of the most important parameters associated with the cardiac cycle are pressures within the left ventricle of the heart. The left ventricle is the chamber of the heart responsible for pumping oxygenated blood throughout the body. The walls of the left ventricle act much like a spring: the more the walls are stretched, the more force the walls may impart to the blood when the ventricle contracts. For example, a normal ventricle is able to expel about 70 mL of blood with a single stroke after being stretched with a pressure (inside the ventricle) of about 10 mmHg. If the walls of the ventricle are under-stretched, the heart delivers less blood when the ventricle contracts. This may happen, for example, when a person has bled so much that the volume of blood left in the body is inadequate to properly fill the heart. The blood pressure then drops significantly since the heart cannot pump out a sufficient amount of blood. Another example is when a person experiences myocardial infarction. These "heart attacks" will sometimes cause a significant portion of the heart to die, and the remaining portion of the heart must compensate for the dead areas to keep the person alive. This often requires that the blood coming into the ventricle stretch the ventricle with more force than normal in order to get the normal amount of flow. In this particular instance, a pressure of 20 mmHg may be required to stretch the left ventricle enough in order to pump the same 70 mL of blood with each stroke.

Several heart-related conditions are directly linked to pressures of blood within the heart. When the heart requires an inordinate filling pressure to pump the same amount of blood that usually would take only 10 mmHg pressure, the patient is considered to have congestive heart failure (CHF). If the heart cannot pump an adequate amount of blood, the patient's blood pressure will fall. However, if the pressures in the left ventricle exceed a certain point, then the blood may back into the lungs, thereby forcing blood and other fluids into the airspaces of the lungs. Under these circumstances, the patient is literally drowning. This condition is commonly referred to as pulmonary edema.

A patient may also have problems that are not heart related that exhibit similar symptoms to those caused by pulmonary edema. For example, fluid in the lungs may also be caused by the kidneys holding excess water, the liver not functioning properly, or the lining of the lungs being damaged, as in the case of drowning victims. When patients are examined in the hospital, it is often impossible to just look at the patient and determine what the problem is.

Heart problems causing symptoms such as those described above may be more easily diagnosed if the filling pressures of the heart are known. When the filling pressures of the heart are high, the heart is likely at fault. If the filling pressures are low, then the heart is usually a victim of other problems. The filling pressure, also referred to as the left ventricular end-diastolic pressure (LVEDP), is the pressure of blood within the left ventricle of the heart immediately following diastole (i.e. the filling cycle of the left ventricle) and before systole (i.e. when the left ventricle contracts to pump blood through the body).

There are primarily two procedures that have been used by physicians to obtain information about pressures within the heart. Both are forms of catheterization, but one approaches the heart from the left side and the other from the right. In a typical "left-heart catheterization," a needle is inserted in the groin, followed by a long flexible tube, the catheter, which is advanced to the heart through a series of blood vessels. The catheter finally passes into the large vessel known as the aorta on the downstream side of the left ventricle. The left-heart catheterization is performed in a specialized lab by a trained cardiologist, who uses special infusible dyes to make parts of the heart visible. A left-heart catheterization provides a means of directly measuring pressure and flow in the heart. This is also the technique used to outline the coronary arteries and determine whether there is a blockage in the arteries in need of a bypass or balloon angioplasty.

In a "right-heart catheterization," a long flexible tube called a Swan-Ganz catheter, is inserted in the neck or under the clavicle and is advanced into the right side of the heart. The pressures that are most desired by physicians are those pressures within the left side of the heart, and blood leaving the right side of the heart must travel to the lungs before returning to the left side of the heart. The catheter therefore includes a balloon attached to its tip, and the balloon is inflated with a small amount of air to allow the catheter to float through the right atrium and right ventricle into the pulmonary artery. The catheter continues to move through the pulmonary artery until it wedges within a distal branch of the pulmonary artery that is smaller in diameter than the balloon. Since the balloon blocks blood flow through the small vessel in which it is wedged, a static column of blood develops between the tip of the catheter and the left atrium. In theory, the pressure measured within this static column of blood upstream of the lungs (i.e. the "wedge pressure") approximates the left atrial pressure. If no obstruction exists between the left atrium and the left ventricle, the wedge pressure may also be a good approximation for the LVEDP. Most of the time, these pressure approximations are accurate enough to allow decisions to be made in the management of critically ill patients.

Left-heart catheterization requires a patient to be very stable, while right-heart catheterization may be performed on critically ill patients. Right-heart catheterization is typically performed in the intensive care unit (ICU), the operating room, or in the emergency room, and is conducted by a specially trained physician. The procedure further requires constant monitoring of heart and lung function, and the catheter may only remain in place for one or two days due to the risk of infection and trauma to the heart. The placement of the Swan-Ganz catheter alone may cost up to two thousand dollars.

Although the information provided by Swan-Ganz catheters is desperately needed, the use of these catheters has fallen out of favor with physicians during the last five years. The procedures are performed much less frequently due to recent studies that suggest the catheters may contribute to complications in patients. Even taking into account the serious illness of patients requiring a Swan-Ganz catheter, the act of using the catheter seems to increase the morbidity and mortality of patients. However, these procedures are still performed when there is no other choice.

A need therefore exists for a system and method that would allow physicians to quickly and accurately determine the condition of a patient's heart without subjecting the patient to the dangers and risks of catheterization. A system is further needed that would allow the health of a patient's heart to be determined in a non-invasive manner that does not require physical penetration of the patient's skin or blood vessels. More specifically, a need exists for a system and method that would inexpensively allow determination of left ventricular pressures within the heart using non-invasive measuring techniques.

BRIEF SUMMARY OF THE INVENTION

The problems presented by determining left ventricular pressures within the heart are solved by the systems and methods of the present invention. In accordance with an embodiment of the present invention, a cardiac pressure monitoring system is provided. The system includes a sensing unit and a processor. The sensing unit is configured to non-invasively measure cardiac parameters of a patient, the cardiac parameters including a mitral valve area, and at least one of a stroke volume of the left ventricle, a left ventricular diastolic filling time and a change in velocity of blood entering the left ventricle over time. The processor is configured to receive the plurality of cardiac parameters and calculate a left ventricular pressure using the measured cardiac parameters.

A method for determining a left ventricular end-diastolic pressure of blood within a left ventricle of a patient is provided according to an embodiment of the present invention. The method includes a step of non-invasively measuring a plurality of cardiac parameters of the patient, including a stroke volume of the left ventricle, a mitral valve area, and a left ventricular diastolic filling time. The method further includes a step of determining the left ventricular end-diastolic pressure using the measured cardiac parameters.

A method for performing real-time measurements of a left ventricular pressure of blood within a left ventricle of a patient is provided according to an embodiment of the present invention. The method includes non-invasively measuring a plurality of cardiac parameters, including a volume of the left ventricle, a velocity of blood entering the left ventricle, and a mitral valve area. The method further includes monitoring a change in velocity of the blood entering the left ventricle over time. The measured cardiac parameters and the change in velocity over time are then used to determine the left ventricular pressure.

A cardiac function diagnostic system is further provided according to an embodiment of the present invention. The system includes a sensing unit configured to non-invasively measure a plurality of cardiac parameters of a left ventricle of a patient, including a mitral valve area and at least one of a stroke volume of the left ventricle, a left ventricular diastolic filling time, a velocity of blood entering the left ventricle, and a change in velocity of blood entering the left ventricle over time. The system further includes a processor that is configured to receive the plurality of cardiac parameters, calculate a left ventricular pressure using the measured cardiac parameters, and compare the left ventricular pressure to a predefined pressure value to assist in the diagnosis of a cardiac function.

A method of diagnosing a cardiac function of a heart is provided according to an embodiment of the present invention. The method includes non-invasively determining a left ventricular pressure of the blood within a left ventricle of the heart. The method further includes comparing the left ventricular pressure to a predefined value to diagnose the cardiac function.

A fluid status diagnostic system is provided according to an embodiment of the present invention. The system includes a sensing unit configured to non-invasively measure a plurality of cardiac parameters of a left ventricle of a patient. The cardiac parameters include a mitral valve area and at least one of a stroke volume of the left ventricle, a left ventricular diastolic filling time, a velocity of blood entering the left ventricle, a maximum velocity of blood entering the left ventricle, and a change in velocity of blood entering the left ventricle over time. The system further includes a processor that is configured to receive the plurality of cardiac parameters and calculate a left ventricular pressure using the measured cardiac parameters. The processor compares the left ventricular pressure to a predefined pressure value to assist in the diagnosis of a fluid status.

A method of diagnosing a fluid status of a patient is provided according to an embodiment of the present invention. The method includes non-invasively determining a left ventricular pressure of blood within a left ventricle of a heart of the patient. The method further includes comparing the left ventricular pressure to a predefined pressure value to diagnose the fluid status.

BRIEF DESCRIPTION OF THE DRAWINGS

FIG. 1 illustrates a graph having a voltage profile, velocity profile, and pressure profile of a normal heart during diastole;

FIG. 2 depicts a graph having a sine wave used to model an E-phase of a cardiac cycle;

DETAILED DESCRIPTION OF THE PREFERRED EMBODIMENT

Figure 3:
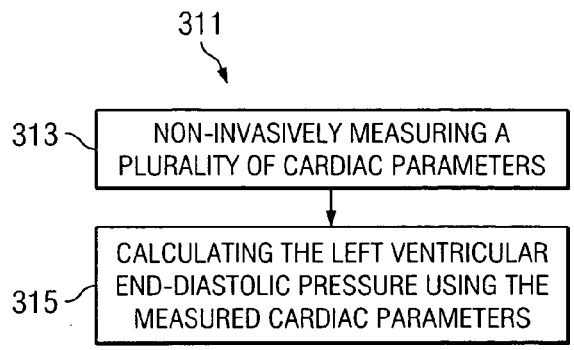
FIG. 3 illustrates a flowchart detailing a method for measuring a left ventricular end-diastolic pressure according to an embodiment of the present invention.

In the following detailed description of the preferred embodiments, reference is made to the accompanying drawings which form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical mechanical, electrical, and software changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The systems and methods of the present invention determine left ventricular pressures by non-invasively measuring certain cardiac parameters associated with a heart. The cardiac parameters may be measured at various times throughout the cardiac cycle of the heart depending on the particular pressure of interest. For example, in at least one embodiment of the present invention, the left ventricular end-diastolic pressure (LVEDP) is determined, which is the pressure of blood within the left ventricle at the end of diastole and just prior to systole. This pressure is also commonly referred to as the filling pressure, and as described previously, represents an important value for determining the overall health of the heart, and more specifically for determining whether the failing heart of a patient is being caused by non-cardiac issues or whether the heart itself is the root of the patient's problem.

The determination of LVEDP according to an embodiment of the present invention is based on the concept of momentum, especially the momentum of blood as it moves into and through the left ventricle. Two equations may be derived to determine an instantaneous pressure within the left ventricle at the end of diastole. The first equation (Equation 1) is based on the principle of momentum, and is derived by considering the typical velocity profile across the mitral valve. Referring to FIG. 1 in the drawings, a typical velocity profile 111 during diastole across the mitral valve is illustrated. During diastole, the velocity across the mitral valve peaks twice, the first peak corresponding to the E phase of the cardiac cycle (i.e. an E phase peak 113) and the second peak corresponding to the A phase (i.e. an A phase peak 115). Also illustrated in FIG. 1 is a voltage profile 121 and a pressure profile 131. Each of the profiles 111, 121, 131 in FIG. 1 are illustrated as a function of time (t), and the profiles are aligned with respect to discrete times during the cardiac cycle. For example, when the velocity profile peaks at the E phase peak 113, it is evident that the corresponding pressure is at a substantially minimum value. The pressure at this particular time corresponds to the LVEDP. The majority of the blood filling the left ventricle occurs during the E phase. During the later A phase, much less is contributed to the development of the filling pressure. Consequently, the majority of the filling pressure (LVEDP) develops in approximately the first one third (⅓) of the filling time (i.e. diastole).

Referring now to FIG. 2, the velocity profile during diastole may be modeled as a sine function, represented by a sine wave 211. Since the LVEDP develops during the E phase, it is the E phase that is modeled. The E phase is represented on the sine wave 211 by a primary region 215 shown in a solid line and a secondary region 217 shown in a broken line. The velocity profile represented by the primary region 215 of the since wave 211 includes a maximum velocity, $v_{max}$. The primary region 215 spans a time period A that is approximately ⅓ of diastole, which corresponds to the amount of time occupied by the E phase. A time period B is representative of the sine wave period, T. A time period C is representative of the total filling time, or diastole.

Mathematically, the primary region 215 of the sine wave 211 may be represented by the following velocity equation:

$$v = v_{max} \sin(\omega t).$$

The angular frequency, $\omega$, is represented by:

$$\omega = \frac{2\pi}{T},$$

where T is the period (see time period B in FIG. 2). Since the E phase and the development of the filling pressure occurs during the first third of the diastolic filling time, $t_D$, (see time period C in FIG. 2), it is this first third that is of interest in determining LVEDP. Therefore, since the E phase corresponds to only half of a complete period of the sine wave (see time period A in FIG. 2), the period may be determined as follows:

$$T \approx \frac{2\Delta t_D}{3}.$$

To determine the LVEDP, the equations for velocity are used with the following equation for momentum:

$$p = mv.$$

where p is the momentum, m is the mass, and v is the velocity. The force equation, in terms of momentum is:

$$F = \frac{dp}{dt} = m\frac{dv}{dt} + v\frac{dm}{dt}.$$

Since the velocity of the blood is zero (i.e. v=0) at the time at which LVEDP is determined, the force equation becomes:

$$F = m\frac{dv}{dt}.$$

Taking advantage of the velocity profile developed above, the derivative of the velocity equation yields dv/dt:

$$v = v_{max} \sin(\omega t), \text{ and}$$

$$\frac{dv}{dt} = \omega v_{max} \cos(\omega t)$$

Now, the equation for force may be more specifically written as:

$$F = m\omega v_{max} \cos(\omega t).$$

Substituting for the angular frequency $\omega$ and the period T yields:

$$F = \frac{3\pi m v_{max}}{\Delta t_D} \cos(3\pi).$$

Solving for the LVEDP yields Equation 1:

$$LVEDP = \frac{F}{A_{mitral}}, \text{ and} \quad \text{[Equation 1]}$$

$$LVEDP = \frac{3\pi\rho(SV)v_{max}}{A_{mitral}\Delta t_D}.$$

Equation 1 has the advantage of using data that may be easily measured and plugged into a calculator for an instant result. The second equation for LVEPD may be similarly used to obtain instant hand calculations of this important pressure and is based more specifically on the concept of impulse, which is the difference in momentum at two different times. Like Equation 1, the calculation of Equation 2 takes advantage of the fact that the flow across the mitral valve of the heart reaches a peak, and then falls off to zero at the precise moment for which it is desired to obtain the LVEDP. The impulse equation is represented mathematically by the following equation:

Impulse=$\Delta p = p_2 - p_1$, where $p_1$ is the momentum at a first time and $p_2$ is the momentum at a second time. At the time the LVEDP is measured, since the velocity of the blood at the second time is zero, $p_2$ equals zero. The continuity equation is then used to relate the velocity of blood flow across the mitral valve to the volume, V, of blood passing the mitral valve:

$$v = \frac{\Delta V}{A_{mitral}(\Delta t)}$$

where v is the velocity of the blood across the mitral valve, $A_{mitral}$ is the area across the mitral valve, and $\Delta t$ is the time over which the volume change is measured.

The average force, $F_{avg}$, exerted by the blood entering the left ventricle may be determined based on its relationship to the change in momentum over time, as represented by the following equation:

$$F_{avg} = \frac{\Delta p}{\Delta t} = \frac{p_2 - p_1}{\Delta t}$$

Since momentum is equal to the mass of an object (i.e. blood) multiplied by the velocity of the object, and since the term $p_2$ equals zero as explained previously, the equation for average force may be rewritten as:

$$F_{avg} = \frac{mv_{max}}{\Delta t},$$

where m is the mass of the blood and $v_{max}$ is the maximum velocity across the mitral valve during diastole. The equation for $v_{max}$ may thus be rewritten as:

$$v_{max} = \frac{SV}{A_{mitral}(\Delta t)},$$

where SV is the stroke volume of the left ventricle. Substituting this equation for $v_{max}$ in the force equation and rewriting m in terms of density, $\rho$, and stroke volume (i.e. m=$\rho \times$SV) yields:

$$F_{avg} = \frac{\rho}{A_{mitral}}\left(\frac{SV}{\Delta t}\right)^2.$$

Solving for LVEDP yields:

$$LVEDP = \frac{F_{avg}}{A_{mitral}},$$

or $$LVEDP = \rho\left(\frac{SV}{A_{mitral}(\Delta t)}\right)^2.$$

As mentioned previously, $\Delta t$ is the time over which the volume change is measured. Referring again to FIGS. 1 and 2, the E phase, during which the LVEDP is developed, represents approximately ⅓ of the total diastolic filling time, $t_D$. The calculation for Equation 2 involves the change in momentum between the time the velocity is zero and the time the velocity is at a maximum (see $v_{max}$ on FIG. 2). This maximum velocity develops within about the first half the E phase, or ⅙ of the total diastolic filling time. Therefore, $\Delta t$ may be represented as:

$$\Delta t = \frac{\Delta t_D}{6},$$

and the LVEDP may be rewritten as:

$$LVEDP = 36\rho\left(\frac{SV}{A_{mitral}(\Delta t_D)}\right)^2. \quad \text{[Equation 2]}$$

If metric values are used to calculate the LVEDP in Equations 1 and 2, the resultant pressure will be obtained in Pascals, which may be converted to the units used in cardiology, mmHg, by multiplying by $7.5006 \times 10^{-3}$.

Once again, Equations 1 and 2 allow a physician or technician to read data directly from a non-invasive measurement apparatus (e.g. echocardiogram apparatus, magnetic resonance imaging (MRI) apparatus, computer-aided tomography (CAT) apparatus, or any other non-invasive measurement apparatus) and then directly calculate the filling pressure using a calculator. Software is not necessarily needed for performing these calculations. However, these equations may be incorporated into the firmware or software of the non-invasive measurement apparatus or a computer or other processing system to allow automatic calculation of the filling pressure.

A third equation, also based on the principles of momentum, allows pressures within the left ventricle to be determined at any time during the cardiac cycle (not only at the end of diastole) based upon non-invasive measurements conducted by a non-invasive measurement apparatus (e.g. an echocardiogram, an MRI, a CAT, or any other apparatus that allows noninvasive measurements of cardiac parameters). As mentioned previously, the momentum equation is represented by:

$$p = mv,$$

where p is the momentum, m is the mass, and v is the velocity. Force, F, may be written in terms of momentum:

$$F = \frac{dp}{dt} = m\frac{dv}{dt} + v\frac{dm}{dt}$$

Velocity, v, may be represented in terms of volume, V:

$$v = \frac{1}{A_{mitral}} \frac{dV}{dt},$$

and $$\frac{dv}{dt} = \frac{1}{A_{mitral}} \frac{d^2V}{dt^2}$$

The mass, m, of blood within the left ventricle may be calculated by multiplying the density, ρ of the blood (approximately 1060 kg/m³) by the volume. Solving the force equation for left ventricular pressure, LVP, in terms of volume of the left ventricle, V, yields:

$$LVP = \frac{\rho}{A_{mitral}^2} \left[ V\frac{d^2V}{dt^2} + \left(\frac{dV}{dt}\right)^2 \right].$$

By using the velocity equation developed earlier and substituting velocity terms for volume, the left ventricular pressure equation may also be represented as follows:

$$LVP = \frac{\rho V}{A_{mitral}} \frac{dv}{dt} + \rho v^2. \qquad \text{[Equation 3]}$$

If LVEDP is desired, the velocity term of the equation is eliminated since v is zero at the time the filling pressure, LVEDP, is calculated. Solving for LVEDP yields Equation 4:

$$LVEDP = \frac{F}{A_{mitral}}, \qquad \text{[Equation 4]}$$

and then $$LVEDP = \left(\frac{\rho SV}{A_{mitral}}\right)\frac{dv}{dt}.$$

Both Equations 3 and 4 require that the change in velocity over time (dv/dt) (i.e. the slope of the velocity, or acceleration) be determined, which would preferably be numerically determined using software associated with the non-invasive measurement apparatus (i.e. echocardiograph, MRI, CAT, or other non-invasive measurement apparatus) or a separate computer or processing system. By using Equation 3, it is possible to obtain real-time blood pressures within the left ventricle at any time during the cardiac cycle.

Referring to FIG. 3, a method 311 of measuring a left ventricular end-diastolic pressure of blood within a left ventricle of a patient according to an embodiment of the present invention is illustrated. The method 311 includes a step 313 of non-invasively measuring a plurality of cardiac parameters of the patient, including a stroke volume of the left ventricle, a mitral valve area, and a left ventricular diastolic filling time. Each of the cardiac parameters is capable of being measured non-invasively, or without physical penetration of the skin or blood vessels of the patient, by an echocardiograph, MRI, CAT, or other measurement apparatus. Echocardiography is the preferred method of measurement since it is less expensive than MRI and CAT techniques. By directing sound waves into a target area of the body (e.g. the left ventricle of the heart) and then capturing the sound waves after being reflected from the target area, the echocardiograph is able to image the target area based on the varying densities of different tissues within the target area. The images developed by the echocardiograph during the cardiac cycle allow determination of the volumes of heart chambers at various times throughout the cardiac cycles (e.g. the stroke volume of the left ventricle), areas of openings between chambers (e.g. the mitral valve area), and time periods associated with the cardiac cycle (i.e. the left ventricular diastolic filling time). If a Doppler echocardiograph is used, the velocity of blood entering the left ventricle, including the maximum velocity of blood entering the left ventricle, may also be measured. The measurement of these types of cardiac parameters may also be easily accomplished using the imaging techniques provided by MRI and CAT.

The method 311 also includes a step 315 of calculating the left ventricular end-diastolic pressure using the measured cardiac parameters. The preferred method of calculating the LVEDP is to use either Equation 1 or Equation 2 described previously because of the simplicity of hand calculation. If real-time pressures are being monitored, the pressure within the ventricle at any time or the LVEDP may be calculated using Equation 3. Equation 4 may also be used to calculate LVEDP. While the specific cardiac parameters used in each of these equations varies slightly, all equations will give a good indication of the LVEDP. The actual process of calculating the LVEDP may be performed manually, by calculator, or by a firmware or software program. If a firmware or software program is used, the program may be integrated into the non-invasive measurement apparatus used to measure the cardiac parameters, or the program may be independently stored and/or operated by a separate computer or processing system such as a personal computer or a handheld device.

Figure 4:
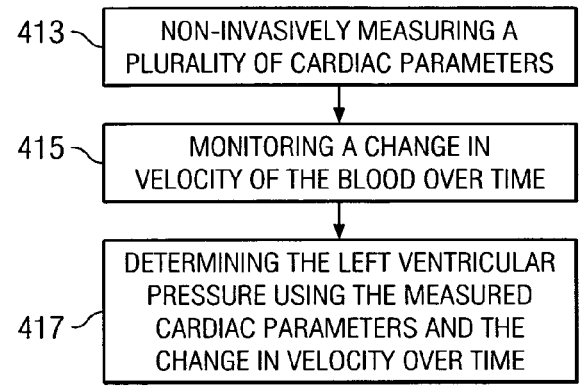
FIG. 4 depicts a flowchart detailing a method for performing real-time measurements of a left ventricular pressure according to an embodiment of the present invention.

Referring to FIG. 4, a method 411 for performing real-time measurements of a left ventricular pressure of blood within a left ventricle of a patient is illustrated according to an embodiment of the present invention. The method 411 includes a step 413 of non-invasively measuring a plurality of cardiac parameters, including without limitation a stroke volume of the left ventricle and a mitral valve area. Each of the cardiac parameters is capable of being measured non-invasively by an echocardiograph, MRI, CAT, or other measuring apparatus. The echocardiograph is the preferred method of measurement since it is less expensive than MRI and CAT techniques.

In another step 415 of the method 411, a change in velocity of the blood entering the left ventricle over time is monitored. In Equations 3 and 4, the change in velocity of the blood over time is represented by the derivative dv/dt. This parameter may also be referred to as the "slope" of the velocity or the acceleration of blood through the left ventricle. This parameter of the heart may be measured using Doppler echocardiography, MRI, CAT or other measurement techniques for determining cardiac blood velocities.

The method 411 further includes a step 417 of determining the left ventricular pressure of the blood using the measured cardiac parameters and the change in velocity over time. The left ventricular pressure may be the pressure of the blood in the left ventricle at any time during the cardiac cycle. For example, this may include the LVEDP measured at the end of diastole, or it may be a pressure measured during systole. These pressure determinations are preferably made in real-time by applying Equation 3 to the cardiac parameters measured at a given time during the cardiac cycle and the slope of the velocity. Since a derivative is involved in Equation 3, it is preferred that the left ventricular pressures are determined using a software or firmware program that is programmed to include Equation 3 or a variation of Equation 3. The program may be integrated into the non-invasive measurement apparatus used to measure the cardiac parameters, or the program may be independently stored and/or operated by a separate computer or processing system such as a personal computer or a handheld device. If only the LVEDP is sought, then Equation 4 may be used in lieu of Equation 3.

Equation 3 allows measurement of pressures within the left ventricle at any time during the cardiac cycle. This capability allows the pressures to be displayed in real-time as cardiac parameters are being measured. This additional data is useful to physicians in obtaining a complete picture of the heart during the cardiac cycle.

Figure 5:
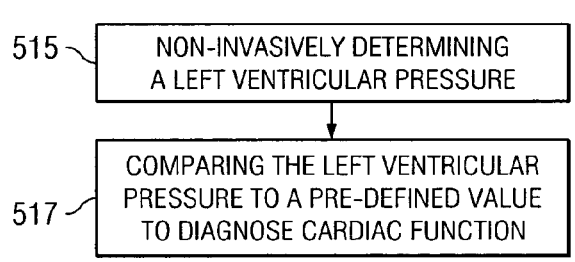
FIG. 5 illustrates a flowchart detailing a method for diagnosing a cardiac function of a heart according to an embodiment of the present invention.

Referring to FIG. 5 in the drawings, a method 511 of non-invasively diagnosing a cardiac function of a patient according to an embodiment of the present invention is illustrated. "Cardiac function" is used generally herein to describe the condition of the heart as it relates to identifying whether or not the heart is experiencing problems. Cardiac function is not meant to be used in a limiting sense and the diagnosis of a cardiac function may refer to identifying a heart-related problem or condition, including without limitation angina, myocardial infarction, CHF, or any other heart-related problem, by non-invasively measuring pressures associated with the heart or vessels surrounding the heart. The diagnosis of a cardiac function may also refer to the determination that no heart-related problem exists.

There are a myriad of heart-related conditions that may be diagnosed if pressures within the left ventricle, especially the LVEDP, are determined. The present invention is believed to aid in the diagnosis of cardiac function and in the cause of common chest pain. One of the most challenging and costly evaluations in the emergency room today is determining the cause of chest pain. Angina, which manifests through a sensation of severe pain and constriction in the chest, is caused by a temporary obstruction (due to constriction, clot formation, or plaque formation) of a blood vessel leading to the heart during periods of peak oxygen demand. This restriction results in a temporary deficiency of oxygen to the heart muscle served by the obstructed vessel. Myocardial infarction involves a complete cessation of blood flow to an area of the heart, which starves that particular area of oxygen, thereby rendering the heart muscle in that area useless if the supply of oxygen-carrying blood is not restored quickly. Myocardial infarction is what is commonly referred to as a "heart attack" and may result in serious illness or the death of the patient.

Congestive heart failure (CHF), while not presenting as chest pain, may result directly from a myocardial infarction. In CHF, the heart is unable to provide an adequate blood supply to the body with normal filling pressures. Typically the contractility of the left ventricle decreases enough that it is unable to "squeeze" hard enough to adequately circulate blood throughout the body. The decreased contractility of the ventricle causes small volume increases in the ventricle to produce relatively large pressure increases. These pressure increases make the LVEDP an excellent determinant of CHF. When the pressures within the ventricle increase substantially, blood may pool in the lungs causing pulmonary edema.

When attempting to diagnose chest pain, great difficulty lies in differentiating between heart-related problems (e.g. angina, myocardial infarction, and other causes of chest pain) and problems originating elsewhere in the body. Angina and myocardial infarction may sometimes be diagnosed by reviewing a patient's heart rhythm on an electrocardiogram machine, due to voltage differences in the patient's cardiac cycle. However, some patients, especially those with diabetes and hypertension, exhibit almost identical electrocardiographs regardless of whether the patient is experiencing angina, myocardial infarction, or no heart problems. For all patients experiencing chest pain, blood tests must be performed to confirm heart-related problems. Evidence of angina or myocardial infarction typically takes about six to eight hours to manifest itself within the blood, and the tests are repeated three times to ensure results. This extended delay in diagnosing and treating patients puts the patient at extreme risk of permanent heart damage or death. This also significantly increases the cost of diagnosis to the patient that has no heart problem.

Referring still to FIG. 5, the method 511 of diagnosing the cardiac function of a heart includes a step 515 of non-invasively determining a left ventricular pressure within a left ventricle of the heart. The left ventricular pressure may be the LVEDP calculated by any of Equations 1 through 4. The step 515 of determining the left ventricular pressure may be accomplished by non-invasively measuring a plurality of cardiac parameters of the patient, which may include a stroke volume of the left ventricle, a mitral valve area, and a left ventricular diastolic filling time. Each of the cardiac parameters is capable of being measured non-invasively, or without physical penetration of the skin or blood vessels of the patient, by echocardiography, MRI, CAT, or other measurement techniques. Echocardiography is the preferred method of measurement since it is less expensive than MRI and CAT. By directing sound waves into a target area of the body (e.g. the left ventricle of the heart) and then capturing the sound waves after being reflected from the target area, the echocardiograph is able to image the target area based on the varying densities of different tissues within the target area. The images developed by the echocardiograph during the cardiac cycle allow determination of the volumes of heart chambers at various times throughout the cardiac cycles (e.g. the stroke volume of the left ventricle), areas of openings between chambers (e.g. the mitral valve area), and time periods associated with the cardiac cycle (i.e. the left ventricular diastolic filling time). If a Doppler echocardiograph is used, the velocity of blood entering the left ventricle, including the maximum velocity of blood entering the left ventricle, may also be measured. The measurement of these types of cardiac parameters may also be easily accomplished using the imaging techniques provided by MRI and CAT.

After determining the necessary cardiac parameters, the left ventricular pressure is calculated. If LVEDP is desired for the diagnosis, calculations may be accomplished with any of Equations 1, 2, 3, or 4. The preferred method of calculating LVEDP is to use either Equation 1 or Equation 2 because of the simplicity of hand calculation. While the specific cardiac parameters used in each of these equations varies slightly, all equations will give a good indication of the LVEDP. If real-time pressures are being monitored, the pressure within the ventricle at any time may be calculated using Equation 3. The process of calculating the LVEDP or the other pressures within the ventricle may be performed manually, by calculator, or by a firmware or software program. If a firmware or software program is used, the program may be integrated into the non-invasive measurement apparatus used to measure the cardiac parameters, or the program may be independently loaded on a separate computer or processing system such as a personal computer or a handheld device.

The method 511 further includes a step 517 of comparing the left ventricular pressure to a pre-defined pressure value to diagnose the cardiac function. As previously explained, diagnosis of the cardiac function of the heart describes the process of determining the health of the heart, and more specifically, determining if any heart-related problems are present.

When a region of the heart lacks oxygen due to angina or myocardial infarction, the heart suffers at least temporary failure. The region of the heart that lacks an adequate blood supply (referred to as ischemia) does not pump, thereby leaving a larger burden on the part of the heart that is still healthy. When the ischemic region of the heart is on the left side of the heart, the LVEDP will typically increase. This is due at least in part to the continued normal operation of the right side of the heart. As the right side continues to pump blood into the left side of the heart, the ischemic region on the left side of the heart cannot maintain normal pumping capability, which results in a buildup of blood and thus pressure within the left chambers of the heart. When the ischemic region of the heart is on the right side of the heart, the LVEDP will typically decrease. Since the right side of the heart is no longer pumping at full capacity, the left side of the heart receives less blood from the right side, thereby resulting in a pressure drop in the left chambers of the heart. Typically, infarctions on the right side of the heart are much less common than infarctions on the left side of the heart.

A healthy heart typically produces an LVEDP of about 10-15 mmHg (a "normal pressure range"). In the method 511 of the present invention, the pre-defined pressure value may be a particular pressure value, or may be a range of values. For example, the pre-defined pressure value may be the normal pressure range. If the LVEDP had been determined, it would then be compared to the normal pressure range. If the LVEDP is between about 10-15 mmHg, the diagnosis would most likely be that the patient is not experiencing heart-related problems and that the current health of the heart is good. If the LVEDP is above about 15 mmHg, the heart is most likely experiencing angina, myocardial infarction, or congestive heart failure. If the LVEDP is below about 10 mmHg, the most likely diagnosis is that a problem elsewhere in the body is affecting the operation of the heart. However, in some cases, the determination of an LVEDP below 10 mmHg may be an indication that a myocardial infarction or other heart-related problem is occurring in the right side of the heart. The ranges and values for the pre-defined pressure value may of course be adjusted depending on the particular medical history and physical characteristics of the patient.

Preliminary verification that the method 511 may be used to diagnose chest pain has yielded favorable results. An emergency room patient who had previously been diagnosed with angina was non-invasively measured using an echocardiogram. The cardiac parameters measured included the stroke volume, the mitral valve area, the maximum velocity, and the diastolic filling time. When the patient was pain free, the LVEDP was calculated to be about 16 mmHg, or close to a normal value. During two different episodes of chest pain, the LVEDP was calculated to be approximately 25 mmHg, thereby indicating angina.

Figure 6:
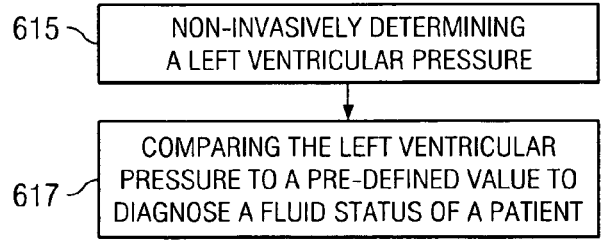
FIG. 6 depicts a flowchart detailing a method for determining a fluid status of a patient according to an embodiment of the present invention.

Referring to FIG. 6, a method 611 of non-invasively diagnosing a fluid status of a patient according to an embodiment of the present invention is illustrated. The diagnosis of the "fluid status" of a patient refers generally to determining the health of the patient with respect to fluid amounts (e.g. volumes) and fluid distributions in the body of the patient. Fluid status is not meant to be used in a limiting sense and the diagnosis of a fluid status may refer to identifying any fluid-related problem or imbalance in the body, including without limitation dehydration, sepsis, pulmonary edema, low blood volume, and shifts in intravascular fluid volumes, such as those caused by extensive burns or trauma. Determining the fluid status may also be used to monitor dialysis patients since removal of too much water from the blood may present serious complications. The diagnosis of a fluid status may also refer to the determination that no fluid-related problem exists.

The method 611 of non-invasively diagnosing a fluid status of a patient includes a step 615 of non-invasively determining a left ventricular pressure within a left ventricle of the heart. The left ventricular pressure may be the LVEDP calculated by any of Equations 1 through 4. The step 615 of determining the left ventricular pressure may be accomplished by non-invasively measuring a plurality of cardiac parameters of the patient, which may include a stroke volume of the left ventricle, a mitral valve area, and a left ventricular diastolic filling time. Each of the cardiac parameters is capable of being measured non-invasively, or without physical penetration of the skin or blood vessels of the patient, by echocardiography, MRI, CAT, or any other measurement techniques. Echocardiography is the preferred method of measurement since it is less expensive than MRI and CAT techniques. By directing sound waves into a target area of the body (e.g. the left ventricle of the heart) and then capturing the sound waves after being reflected from the target area, the echocardiograph is able to image the target area based on the varying densities of different tissues within the target area. The images developed by the echocardiograph during the cardiac cycle allow determination of the volumes of heart chambers at various times throughout the cardiac cycles (e.g. the stroke volume of the left ventricle), areas of openings between chambers (e.g. the mitral valve area), and time periods associated with the cardiac cycle (i.e. the left ventricular diastolic filling time). If a Doppler echocardiograph is used, the velocity of blood entering the left ventricle, including the maximum velocity of blood entering the left ventricle, may also be measured. The measurement of these types of cardiac parameters may also be easily accomplished using the imaging techniques provided by MRI and CAT.

After determining the necessary cardiac parameters, the left ventricular pressure is calculated. If LVEDP is desired for the diagnosis, calculations may be accomplished with any of Equations 1, 2, 3, or 4. The preferred method of calculating LVEDP is to use either Equation 1 or Equation 2 because of the simplicity of hand calculation. While the specific cardiac parameters used in each of these equations varies slightly, all equations will give a good indication of the LVEDP. If real-time pressures are being monitored, the pressure within the ventricle at any time may be calculated using Equation 3. The process of calculating the LVEDP or the other pressures within the ventricle may be performed manually, by calculator, or by a firmware or software program. If a firmware or software program is used, the program may be integrated into the non-invasive measurement apparatus used to measure the cardiac parameters, or the program may be independently stored and/or operated by a separate computer or a processing system such as a personal computer or a handheld device.

The method 611 further includes a step 617 of comparing the left ventricular pressure to a pre-defined pressure value to diagnose the fluid status of the patient. As previously explained, diagnosis of the fluid status of the patient describes the process of determining the health of the patient with respect to fluid amounts and distributions in the body, and more specifically determining if any fluid-related problems are present.

Fluids exist throughout the body and may be categorized as intravascular fluids, interstitial fluids, and intracellular fluids. Intravascular fluids are those fluids within the circulatory vessels of the body such as the blood vessels. Intracellular fluids are those fluids located within the cells of the body. Interstitial fluids are those fluids that are not otherwise characterized as intravascular fluids or intracellular fluids. A major component of almost all fluids in the body is water.

Certain problems or occurrences may cause a decrease in the fluid volume of a patient. In most cases, a decrease in the volume of a body fluid will cause the blood to lose water volume. For example, when a patient has intestinal or kidney problems for an extended period of time, excessive diarrhea or urination will often result in dehydration, which then results in a loss of blood water volume. Dehydration may also occur if the patient experiences a high fever for an extended period of time. For a patient requiring dialysis, blood is circulated to filter out impurities that cannot be removed by the patient's kidneys. Water volumes in a dialysis patient typically increase significantly between treatments, sometimes enough that the patient's weight will increase greatly. The dialysis process removes water from the patient, but it may be difficult to predict how much water needs to be removed during any given treatment. Technicians estimate the amount of water that needs to be removed and then monitor the patient's blood pressure during the dialysis process. As the water volume decreases in the patient, the blood pressure may fall rapidly. Determining when to stop removing water may be very difficult, and a patient's blood water volume may rapidly drop to a level that is not healthy for the patient.

Other fluid-related problems include sepsis. When an infection develops within the blood of a patient, the blood vessels react by dilating. The dilation of these vessels effectively increases the volume of the "container" in which the blood resides, which results in symptoms mimicking low blood volume.

A healthy heart typically produces an LVEDP of about 10-15 mmHg (a "normal pressure range"). In the method 611 of the present invention, the pre-defined pressure value may be a particular pressure value, or may be a range of values. For example, the pre-defined pressure value may be the normal pressure range. If the LVEDP has been determined, it may then be compared to the normal pressure range. If the LVEDP is between about 10-15 mmHg, the diagnosis would most likely be that the patient is not experiencing fluid-related problems. However, an LVEDP below about 10 mmHg most likely indicates a fluid-related (non-heart related) problem. For the conditions described above, such as dehydration, sepsis, and low blood volume, the decreased volume of blood returning to the heart cause the pressures in the left ventricle to drop. Although an LVEDP below about 10 mmHg may be an indication of a right-heart myocardial infarction, the more likely diagnosis is a fluid-related problem, especially in the absence of chest pain. The ranges and values for the pre-defined pressure value may of course be adjusted depending on the particular medical history and physical characteristics of the patient.

Figure 7:
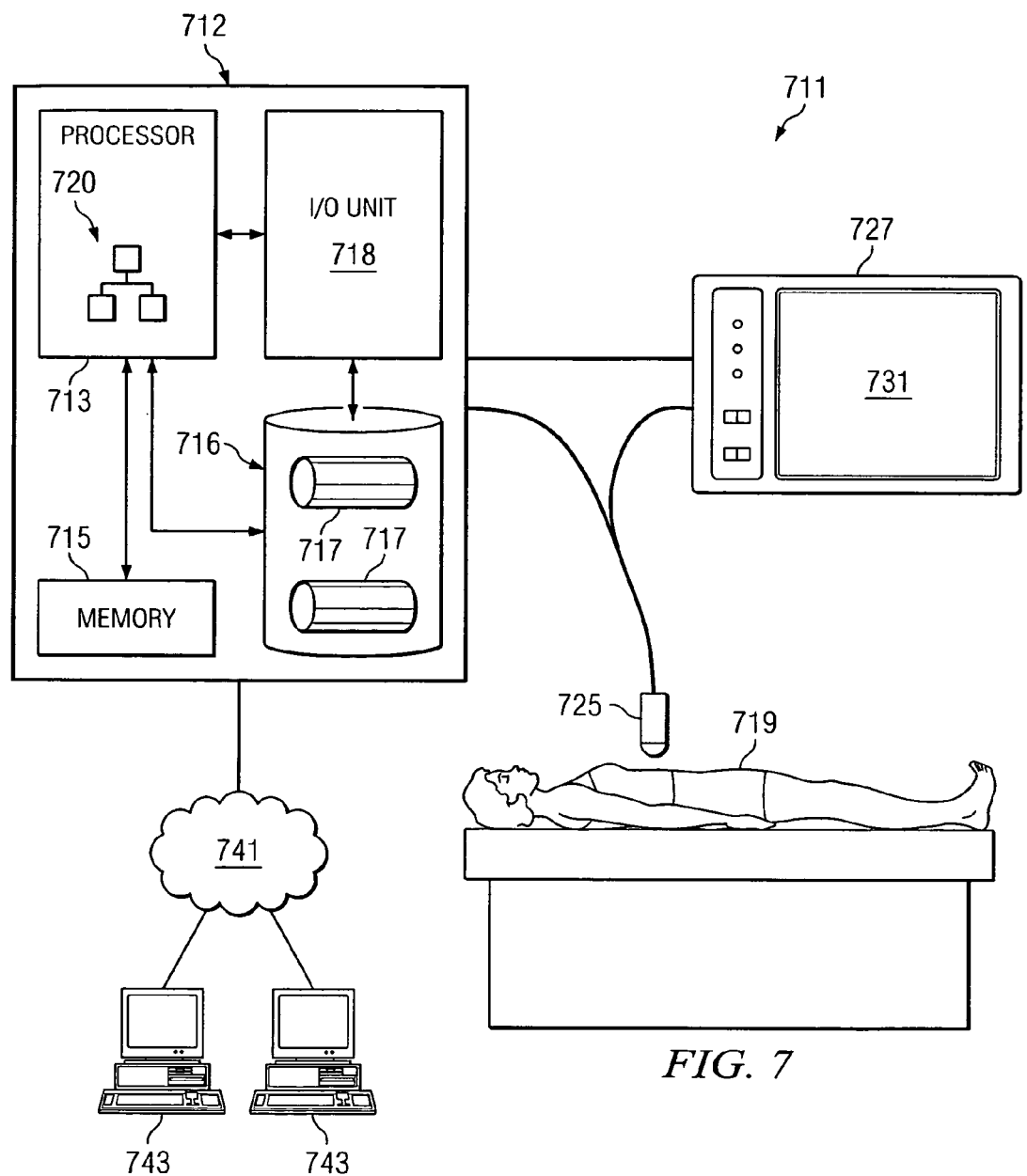
FIG. 7 illustrates a schematic of a cardiac pressure monitoring system according to an embodiment of the present invention.

Referring now to FIG. 7, a cardiac pressure monitoring system 711 according to an embodiment of the present invention includes a computer or other processing system 712 having a processor 713 operably connected to a memory medium 715, which may include RAM, ROM, or any other memory medium. The processor 713 may be composed of one or more processors in communication with each other. The computer 712 further includes a storage device 716 operably connected to the processor 713, the storage device 716 having at least one database 717 or data reservoir. The storage device may include a hard drive, magnetic media, optical media, or any other storage medium capable of storing data. The computer 712 further includes at least one input/output device 718, such as a keyboard, a mouse, or a display monitor. A computer software program 720 is operably associated with the processor 713 such that the instructions of the computer software program 720 may be executed by the processor 713. It should be noted that the computer software program 720 may be permanently stored within storage device 716 and then at least partially loaded into memory medium 715 during operation of the computer 712. The computer software program 720 would then be executed by the processor 713, which communicates with the memory medium 715.

Preferably, the storage device 716 is capable of receiving and storing a plurality of non-invasively measured cardiac parameters associated with a left ventricle of a patient 719. The cardiac parameters are preferably measured by a sensing unit such as a sensor 725 associated with a measuring apparatus 727 such as an echocardiograph, MRI, or CAT apparatus. For example, the sensing unit may be a sonic transducer from an echocardiograph machine, or the sensing unit may be an RF receiver coil associated with an MRI machine. It is important to note that the term sensing unit is not meant to be limiting and may include the sensor itself, the sensor and the associated hardware that are part of the measuring apparatus, or any other sensing unit capable of measuring the cardiac parameters. The processor 713 may be used in conjunction with the storage device 716 to manage the collection and storage of the cardiac parameters. Measuring apparatus 727 may include a monitor 731 that is either integral to or separate from the measuring apparatus 727. The monitor 731 and/or the input/output device 718 may be used to display an output resulting from the methods discussed herein. The output may include a single cardiac pressure, such as LVEDP, or may include a plurality of cardiac pressures such as those that may be determined from a method similar to that illustrated in FIG. 4. The output displayed may include a tabular or other type of listing of cardiac pressure, or may include a graphical representation of the cardiac pressures similar to the pressure profile 131 of FIG. 1.

After receiving the cardiac parameters, the system 711 determines a left ventricular pressure by having the processor 713 calculate the pressure using either Equation 1, 2, 3, or 4. The particular cardiac parameters that are measured may depend on the equation that is used to calculate the pressure. For example, if the left ventricular pressure at any given time of the cardiac cycle is desired, Equation 3 may be used to generate and display real-time pressures within the left ventricle. If the left ventricular end-diastolic pressure is desired, any of the four equations may be used. For example, Equation 1 may be used in conjunction with the measured cardiac parameters of stroke volume, mitral valve area, left ventricular diastolic filling time, and maximum velocity.

While the computer 712 may be integrated within any of the measuring devices (e.g. echocardiograph apparatus, MRI apparatus, or CAT apparatus) mentioned herein, it is also possible that the computer 712 may be separately housed and electronically or wirelessly connected to the measuring apparatus 727 as shown in FIG. 7. It is of course possible to connect the computer 712 and/or the measuring apparatus 727 to a network 741, which may include without limitation a wide area network (WAN), a local area network (LAN), the Internet, or any other network. The network 741 would allow communication with other computing or display devices 743 to allow remote monitoring or diagnosis of the patient 719.

The system 711 of the present invention may also be used as a cardiac function diagnostic system to diagnose a cardiac function of the patient 719 according to a method similar to method 511 illustrated in FIG. 5. If used as a cardiac function diagnostic system, the system 711 may measure a plurality of cardiac parameters with the sensing unit. The processor 713 may receive the plurality of cardiac parameters, calculate a left ventricular pressure using the measured cardiac parameters, and compare the left ventricular pressure to a predefined pressure value for assisting in the diagnosis of the cardiac function.

The system 711 of the present invention may also be used as a fluid status diagnostic system to diagnose a fluid status of the patient 719 according to a method similar to the method 611 illustrated in FIG. 6. If the system 711 were used as a fluid status diagnostic system, a plurality of cardiac parameters may be measured by the sensing unit. The processor 713 may receive the plurality of cardiac parameters, calculate a left ventricular pressure using the measured cardiac parameters, and compare the left ventricular pressure to a predefined pressure value for assisting in the diagnosis of the fluid status of the patient 719.

Test Results

Preliminary test results for determining the LVEDP using Equation 1 have produced excellent results. The calculated pressure using non-invasively measured cardiac parameters was compared with pressures obtained using Swan-Ganz catheters. The data collected, measured, and calculated for eleven patients is illustrated in Table 1. Each wedge pressure was measured using the Swan-Ganz catheter at approximately the same time that the cardiac parameters were measured using non-invasive means. Patient 5 exhibited the only anomaly, but it is believed that valve stenosis may have contributed to the disparity in the wedge pressure and the calculated pressure for this patient.

TABLE 1

| | CARDIAC PARAMETERS | | | | | |
|---|---|---|---|---|---|---|
| Patient | Stroke Volume (ml) | Mitral Valve Area (cm$^3$) | Filling Time (s) | Peak Velocity (m/s) | Calculated LVEDP (mmHg) | Wedge Pressure (mmHg) |
| 1 | 70 | 5.9 | 0.49 | 0.69 | 13 | 14 |
| 2 | 61 | 6 | 0.46 | 0.66 | 11 | 10 |
| 3 | 76 | 4 | 0.37 | 0.56 | 22 | 24 |
| 4 | 72 | 5 | .035 | 0.6 | 19 | 17 |
| 5 | 45 | 1.1 | 0.55 | 0.77 | 43 | 23 |
| 6 | 75 | 5.5 | 0.44 | 0.6 | 14 | 16 |
| 7 | 72 | 5 | 0.4 | 0.75 | 20 | 19 |
| 8 | 55 | 3.9 | 0.38 | 0.8 | 22 | 22 |
| 9 | 69 | 5 | 0.45 | 0.6 | 14 | 13 |
| 10 | 73 | 3.9 | 0.44 | 0.65 | 21 | 23 |
| 11 | 80 | 5.5 | 0.31 | 0.77 | 27 | 24 |

The systems and methods of the present invention allow left ventricular pressures to be determined by non-invasively measuring selected cardiac parameters associated with a patient's heart. By using non-invasive measuring techniques such as echocardiography, Doppler echocardiography, MRI, and CAT to measure cardiac parameters such as the left ventricular stroke volume, the mitral valve area, the left ventricular diastolic filling time, and the velocity of blood entering the left ventricle, the pressure of blood within the left ventricle may be determined.

Although many of the examples discussed herein are applications of the present invention to the left ventricle of a human heart, the methods and systems of the present invention also may be applied to other chambers of the heart. In order to determine other important values associated with the flow of blood through the heart, the non-invasive measuring techniques would be directed to the specific area of interest to determine cardiac parameters associated with that area. The principles of momentum may be adapted and applied to those areas of interest to determine pressures or other values that are not otherwise non-invasively obtainable. It should also be noted that use of the systems and methods of the present invention is not limited to the left ventricles and hearts of humans, but also may be applied to other animals having blood flow characteristics that may be determined non-invasively. In this regard, the term "patient" used herein and throughout the claims may refer to either a human or another animal for which cardiac pressure determination is desired.

While the systems and methods of determining left ventricular pressures according to the present invention are well adapted to diagnosing the cardiac function and fluid status of a patient, the determination of left ventricular pressures may also be used to diagnose other problems (or lack of problems) experienced by a patient. It is contemplated that the systems and methods may be used to diagnose any problems that would be detectable by the use of a Swan-Ganz catheter or other invasive procedures used to determine cardiac pressures.

It should be apparent from the foregoing that an invention having significant advantages has been provided. While the invention is shown in only a few of its forms, it is not just limited but is susceptible to various changes and modifications without departing from the spirit thereof.

I claim:

1. A cardiac pressure monitoring system comprising:
    a sensing unit configured to non-invasively measure a plurality of cardiac parameters of a patient, the cardiac parameters including a mitral valve area, and at least one of a stroke volume of a left ventricle of the patient, a left ventricular diastolic filling time, and a change in velocity of blood entering the left ventricle over time; and
    a processor configured to receive the plurality of cardiac parameters and calculate a left ventricular pressure using the measured cardiac parameters.

2. The system according to claim 1 further comprising a memory unit configured to store at least one of the cardiac parameters.

3. The system according to claim 1 further comprising a display unit configured to display the left ventricular pressure.

4. The system according to claim 1, wherein:
    the left ventricular pressure is a left ventricular end-diastolic pressure; and
    the processor calculates the left ventricular end-diastolic pressure by using a formula:

$$LVEDP = 36\rho \left( \frac{SV}{A_{mitral}(\Delta t_D)} \right)^2,$$

where LVEDP is the left ventricular end-diastolic pressure, ρ is a density of blood; SV is the stroke volume, $A_{mitral}$ is the mitral valve area, and $\Delta t_D$ is the left ventricular diastolic filling time.

5. The system according to claim 1, wherein:
the left ventricular filling time is measured; and
the plurality of cardiac parameters further includes a maximum velocity of the blood entering the left ventricle.

6. The system according to claim 5, wherein:
the left ventricular pressure is a left ventricular end-diastolic pressure; and
the processor calculates the left ventricular end-diastolic pressure by using a formula:

$$LVEDP = \frac{3\pi \rho (SV) v_{max}}{A_{mitral} \Delta t_D},$$

where LVEDP is the left ventricular end-diastolic pressure, ρ is a density of blood, SV is the stroke volume, $v_{max}$ is the maximum velocity of blood entering the left ventricle, $A_{mitral}$ is the mitral valve area, and $\Delta t_D$ is the left ventricular diastolic filling time.

7. The system according to claim 1, wherein the processor calculates the left ventricular pressure by using a formula:

$$LVP = \frac{\rho V}{A_{mitral}} \frac{dv}{dt} + \rho v^2,$$

where LVP is the left ventricular pressure, ρ is a density of blood; V is a volume of the left ventricle, $A_{mitral}$ is the mitral valve area, v is a velocity of blood entering the left ventricle, and $$\frac{dv}{dt}$$

is the change in velocity over time.

8. The system according to claim 1, wherein the sensing unit is a sonic sensor associated with an echocardiogram apparatus.

9. The system according to claim 1, wherein the sensing unit is a magnetic resonance imaging (MRI) apparatus.

10. The system according to claim 1, wherein the sensing unit is a computer aided tomography (CAT) scan apparatus.

11. In an electronic system, in which at least one computer monitors cardiac pressures within a heart of patient, a memory medium having software programmed to:
receive a plurality of non-invasively measured cardiac parameters associated with a left ventricle of the patient, the cardiac parameters including a mitral valve area, and at least one of a stroke volume of a left ventricle of the patient, a left ventricular diastolic filling time, and a change in velocity of blood passing through the left ventricle over time; and
determine a left ventricular pressure using the measured cardiac parameters.

12. The system according to claim 11, wherein the left ventricular pressure is a left ventricular end-diastolic pressure and determining said pressure further comprises calculating the left ventricular end-diastolic pressure using a formula:

$$LVEDP = 36\rho \left( \frac{SV}{A_{mitral}(\Delta t_D)} \right)^2$$

where LVEDP is the left ventricular end-diastolic pressure, ρ is a density of blood; SV is the stroke volume, $A_{mitral}$ is the mitral valve area, and $\Delta t_D$ is the left ventricular diastolic filling time.

13. The system according to claim 11, wherein:
the left ventricular diastolic filling time is measured; and
the plurality of cardiac parameters further includes a maximum velocity of the blood entering the left ventricle.

14. The system according to claim 13, wherein the left ventricular pressure is a left ventricular end-diastolic pressure and determining said pressure further comprises calculating the left ventricular end-diastolic pressure using a formula:

$$LVEDP = \frac{3\pi \rho (SV) v_{max}}{A_{mitral} \Delta t_D}$$

where LVEDP is the left ventricular end-diastolic pressure, ρ is a density of blood; SV is the stroke volume, $v_{max}$ is the maximum velocity of blood, $A_{mitral}$ is the mitral valve area, and $\Delta t_D$ is the left ventricular diastolic filling time.

15. The system according to claim 11, wherein the left ventricular pressure is determined by calculating the left ventricular pressure using a formula:

$$LVP = \frac{\rho V}{A_{mitral}} \frac{dv}{dt} + \rho v^2$$

where LVP is the left ventricular pressure, ρ is the density of blood; V is a volume of the left ventricle, $A_{mitral}$ is the mitral valve area, v is the velocity of blood entering the left ventricle, and $$\frac{dv}{dt}$$

is the change in velocity over time.

16. The system according to claim 11, wherein the cardiac parameters are measured using an echocardiogram apparatus.

17. The system according to claim 11, wherein the cardiac parameters are measured using a magnetic resonance imaging (MRI) apparatus.

18. The system according to claim 11, wherein the cardiac parameters are measured using a computer aided tomography (CAT) scan apparatus.

19. At least one computer programmed to execute a process for monitoring cardiac pressures within a heart of a patient, the process comprising:
receiving a plurality of non-invasively measured cardiac parameters associated with a left ventricle of the patient, the cardiac parameters including a mitral valve area, and at least one of a stroke volume of the left ventricle of the patient, a left ventricular diastolic filling time, and a change in velocity of blood entering the left ventricle over time; and
determining a left ventricular pressure using the measured cardiac parameters.

20. The computer according to claim 19, wherein the left ventricular pressure is a left ventricular end-diastolic pressure and determining said pressure further comprises calculating the left ventricular end-diastolic pressure using a formula:

$$LVEDP = 36\rho\left(\frac{SV}{A_{mitral}(\Delta t_D)}\right)^2,$$

where LVEDP is the left ventricular end-diastolic pressure, ρ is a density of blood; SV is the stroke volume, $A_{mitral}$ is the mitral valve area, and $\Delta t_D$ is the left ventricular diastolic filling time.

21. The computer according to claim 19, wherein:
the left ventricular diastolic filling time is measured; and
the plurality of cardiac parameters further includes a maximum velocity of the blood entering the left ventricle.

22. The computer according to claim 21, wherein the left ventricular pressure is a left ventricular end-diastolic pressure and determining said pressure further comprises calculating the left ventricular end-diastolic pressure using a formula:

$$LVEPD = \frac{3\pi\rho(SV)v_{max}}{A_{mitral}\Delta t_D},$$

where LVEDP is the left ventricular end-diastolic pressure, ρ is a density of blood; SV is the stroke volume, $A_{mitral}$ is the mitral valve area, and $\Delta t_D$ is the left ventricular diastolic filling time.

23. The computer according to claim 19, wherein determining the left ventricular pressure further comprises calculating the left ventricular pressure using a formula:

$$LVP = \frac{\rho V}{A_{mitral}}\frac{dv}{dt} + \rho v^2,$$

wherein LVP is the left ventricular pressure, ρ is a density of blood; V is a volume of the left ventricle, $A_{mitral}$ is the mitral valve area, v is the velocity of blood entering the left ventricle, and $$\frac{dv}{dt}$$

is the change in velocity over time.

24. The computer according to claim 19, wherein the cardiac parameters are measured using an echocardiogram apparatus.

25. The computer according to claim 19, wherein the cardiac parameters are measured using a magnetic resonance imaging (MRI) apparatus.

26. The computer according to claim 19, wherein the cardiac parameters are measured using a computer aided tomography (CAT) scan apparatus.

27. A cardiac function diagnostic system comprising:
a sensing unit configured to non-invasively measure a plurality of cardiac parameters associated with a left ventricle of a patient, the cardiac parameters including a mitral valve area, and at least one of a stroke volume of the left ventricle, a left ventricular diastolic filling time, a velocity of blood entering the left ventricle, a maximum velocity of blood entering the left ventricle, and a change in velocity of blood entering the left ventricle over time; and
a processor configured to receive the plurality of cardiac parameters, calculate a left ventricular pressure using the measured cardiac parameters, and compare the left ventricular pressure to a predefined pressure value for assisting in the diagnosis of a cardiac function.

28. The system according to claim 27, wherein the diagnosis of the cardiac function is used to identify the existence of at least one of angina, myocardial infarction, and congestive heart failure.

29. The system according to claim 27, wherein the diagnosis of the cardiac function is used to determine that no heart-related problems exist.

30. The system according to claim 27, wherein the cardiac parameters are measured using at least one of an echocardiogram apparatus, a magnetic resonance imaging (MRI) apparatus, and a computer aided tomography (CAT) scan apparatus.

31. The system according to claim 27, wherein the processor calculates the left ventricular pressure by calculating a left ventricular end-diastolic pressure using a formula:

$$LVEDP = 36\rho\left(\frac{SV}{A_{mitral}(\Delta t_D)}\right)^2,$$

wherein LVEDP is the left ventricular end-diastolic pressure, ρ is a density of blood; SV is the stroke volume, $A_{mitral}$ is the mitral valve area, and $\Delta t_D$ is the left ventricular diastolic filling time.

32. The system according to claim 27, wherein the processor calculates the left ventricular pressure by calculating a left ventricular end-diastolic pressure using a formula:

$$LVEDP = \frac{3\pi\rho(SV)v_{max}}{A_{mitral}\Delta t_D},$$

where LVEDP is the left ventricular end-diastolic pressure, ρ is a density of blood; SV is the stroke volume, $v_{max}$ is the maximum velocity of blood, $A_{mitral}$ is the mitral valve area, and $\Delta t_D$ is the left ventricular diastolic filling time.

33. The system according to claim 27, wherein the processor calculates the left ventricular pressure using a formula:

$$LVP = \frac{\rho V}{A_{mitral}}\frac{dv}{dt} + \rho v^2,$$

where LVP is the left ventricular pressure, ρ is a density of blood; V is a volume of the left ventricle, $A_{mitral}$ is the mitral valve area, v is the velocity of blood entering the left ventricle, and $$\frac{dv}{dt}$$

is the change in velocity over time.

* * * * *